US007083712B2

(12) United States Patent
Morita et al.

(10) Patent No.: US 7,083,712 B2
(45) Date of Patent: Aug. 1, 2006

(54) FAIL JUDGING METHOD FOR ANALYSIS AND ANALYZER

(75) Inventors: Yoshimitsu Morita, Kyoto (JP); Teppei Shinno, Onsen (JP)

(73) Assignees: ARKRAY, Inc., Kyoto (JP); Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/496,209

(22) PCT Filed: Nov. 18, 2002

(86) PCT No.: PCT/JP02/12035

§ 371 (c)(1),
(2), (4) Date: May 19, 2004

(87) PCT Pub. No.: WO03/044514

PCT Pub. Date: May 30, 2003

(65) Prior Publication Data

US 2005/0000829 A1   Jan. 6, 2005

(30) Foreign Application Priority Data

Nov. 20, 2001   (JP)   ............................. 2001-355324

(51) Int. Cl.
*G01F 1/64* (2006.01)

(52) U.S. Cl. .............. 205/775; 205/777.5; 204/403.01; 204/401

(58) Field of Classification Search ................ 204/403.01–403.14, 416–418, 401 R; 205/775, 205/777.5–778, 787, 789, 792; 422/50, 52, 422/58.1, 82.01–82.03, 82.04–82.13, 83
See application file for complete search history.

(56) References Cited

U.S. PATENT DOCUMENTS

| 3,786,352 A | * | 1/1974 | Woods et al. ................ 324/110 |
| 4,626,413 A | * | 12/1986 | Blades et al. .................. 422/78 |
| 4,931,402 A | * | 6/1990 | Abplanalp ................ 435/287.3 |
| 5,352,351 A | | 10/1994 | White et al. ........... 204/403.04 |
| 2001/0042683 A1 | | 11/2001 | Musho et al. .......... 204/403.14 |

FOREIGN PATENT DOCUMENTS

EP   0922954 A2  *   6/1999

(Continued)

OTHER PUBLICATIONS

English language translation of JP 4-361157 A (patent published on Dec. 14, 1992).*

(Continued)

*Primary Examiner*—Alex Noguerola
(74) *Attorney, Agent, or Firm*—Hamre, Schumann, Mueller & Larson, P.C.

(57) ABSTRACT

An analyzer (A) includes a measurer (42) for measuring an electro-physical quantity of a sample, and an acceleration measurer (43) for computing the acceleration of change of the electro-physical quantity such as a current measured by the measurer (42). The fail determination as to whether or not a predetermined condition necessary for performing analysis of the sample is satisfied is made based on the acceleration computed by the acceleration measurer (43). As a result, the fail determination in the analysis process of the sample can be performed accurately.

11 Claims, 6 Drawing Sheets

FOREIGN PATENT DOCUMENTS

| | | |
|---|---|---|
| JP | 60-159642 | 8/1985 |
| JP | 64-23150 | 1/1989 |
| JP | 4-357452 | 12/1992 |
| JP | 4-361157 | 12/1992 |
| JP | 6-109688 | 4/1994 |
| JP | 8-502589 | 3/1996 |
| JP | 9-264875 | 10/1997 |
| JP | 2001-66274 | 3/2001 |
| JP | 2001-66279 | 3/2001 |

OTHER PUBLICATIONS

English language translation of JP 9-264875 (patent published on Oct. 7, 1997).*

* cited by examiner

Prior Art

FAIL JUDGING METHOD FOR ANALYSIS AND ANALYZER

This application is 371 of PCT/JP02/12035, filed on Nov. 18, 2002, which clams priority from JP 2001355324, filed on Nov. 20, 2001.

TECHNICAL FIELD

The present invention relates to a fail judging method to determine whether or not conditions for performing analysis are right in the analysis of a sample such as the measurement of the glucose level or cholesterol level in blood sample. It also relates to an analyzer for performing such a fail judging method.

BACKGROUND ART

As a method for measuring the concentration of a particular component in a sample such as blood, an electrochemical method is known which utilizes a biosensor provided with a reagent layer and a pair of electrodes. In this method, the sample is introduced to the reagent layer to cause the particular component in the sample to react with a component in the reagent layer. On the other hand, a voltage is applied to the reagent layer by utilizing the electrodes, and the current between the electrodes is measured. The current changes in accordance of the degree of the reaction. Further, the degree of reaction depends on the concentration of the particular component in the sample. The concentration of the particular component in the sample can be computed based on the measurements of the current.

In such analysis, it is desirable that whether or not conditions necessary for performing the analysis are satisfied can be checked in advance. For instance, when the amount of the sample introduced to the reagent layer is insufficient, accurate analysis results cannot be obtained. Further, accurate analysis results may not be obtained due to a defect of the biosensor. When the analysis is carried out without noticing such a fail condition, the user may believe such inaccurate analysis results to be accurate.

JP-B-2800981 discloses a method for detecting such a fail condition as described above. In this method, fail detection is performed by applying a voltage across a pair of electrodes of a biosensor and measuring the current between the electrodes. FIG. 8 shows the change of the current in this method. As shown in the figure, the current between the electrodes continues to increase after a time point indicated by the reference sign n1 at which a sample is introduced to the reagent layer. When the current value exceeds a predetermined threshold value at the time point ta, the introduction of the sample is detected. The rate at which the current increases immediately after the sample introduction depends on the amount of the sample introduced to the reagent layer. The smaller the amount of introduced sample is, the lower the rate at which the current increases. Subsequently, the current at a time point tb after a predetermined period T has elapsed since the time point ta is measured. When the measured current is higher than a predetermined second threshold value as shown in the figure, it is determined that the amount of introduced sample is sufficient. On the other hand, when the measured current is no higher than the second threshold value, it is determined that the amount of introduced sample is insufficient.

In this way, in the prior art method, fail determination is made based on the difference between two current values at predetermined time points. In other words, the determination is made based on the slope of the curve representing the current change at a predetermined time point, i.e., the rate of the current change.

However, the prior art method has following problems.

Although the rate of the change of the current flowing between the electrodes varies depending on the amount of introduced sample as noted above, the variation of the rate of the current change is not sufficiently large when the change of the amount of the sample introduced to the reagent layer is small. Therefore, in the prior art method, it is sometimes difficult to accurately determine whether or not the amount of introduced sample is sufficient. In the prior art method, to eliminate the possibility that the amount of introduced sample is erroneously determined to be sufficient although it is actually insufficient, an excessively large value need be set as the second threshold value Th2. In such a case, however, there is a possibility that the amount of introduced sample is often determined to be insufficient although it is actually sufficient.

DISCLOSURE OF THE INVENTION

An object of the present invention is to provide a fail judging method capable of eliminating or lessening the above-described problems. Another object of the present invention is to provide an analyzer capable of properly performing such a fail judging method.

According to a first aspect of the present invention, there is provided a fail judging method to determine whether or not a predetermined condition necessary for performing analysis of a sample is satisfied by measuring an electro-physical quantity of the sample. The method comprises computing an acceleration of change of the electro-physical quantity and determining whether or not the predetermined condition is satisfied based on the acceleration.

In the present invention, the "electro-physical quantity" refers to current, voltage or variation of charge for example. The "acceleration of change of the electro-physical quantity" refers to a variation, per small unit time, of the rate of change of the electro-physical quantity. The "rate of change of the electro-physical quantity" refers to a variation, per small unit time, of the electro-physical quantity.

In the fail judging method according to the present invention, whether or not a required amount of the sample is supplied may be determined based on the acceleration.

In the present invention, the fail determination is made based on the acceleration of change of an electro-physical quantity, and the acceleration is obtained by differentiating the rate of change of the electro-physical quantity. Therefore, even when the rate of change of the electro-physical quantity does not vary greatly in spite of the change of a condition for the analysis process, the acceleration of change of the electro-physical quantity may vary greatly. Therefore, the acceleration of change of the electro-physical quantity can be utilized as a parameter which varies greatly in response to a slight change of the condition for the sample analysis. Therefore, by utilizing the acceleration of change of the electro-physical quantity as a parameter for the fail determination, whether or not a predetermined condition for performing the sample analysis is satisfied can be determined more accurately than with the prior art method.

According to a second aspect of the present invention, there is provided a fail judging method to determine whether or not a predetermined condition necessary for performing analysis of a sample is satisfied, the analysis comprising causing the sample to react with a predetermined reagent while applying a voltage to the sample and the reagent to cause a current to flow and computing a concentration of a particular component in the sample based on the current. The method comprises computing an acceleration of change of the current at a time point at which the current reaches a predetermined value after the sample is introduced to the reagent layer, and determining whether or not the predetermined condition necessary for performing the analysis is satisfied based on the acceleration.

In the present invention, the determination step may comprise comparing the acceleration with a predetermined threshold value and determining that the predetermined condition is not satisfied when the acceleration is smaller than the threshold value.

According to a third aspect of the present invention, there is provided an analyzer provided with a measurer for measuring an electro-physical quantity of a sample. The analyzer comprises an acceleration measurer for computing an acceleration of change of the electro-physical quantity measured by the measurer.

Preferably, the analyzer further comprises a determiner for determining whether or not a predetermined condition necessary for performing analysis is satisfied based on the acceleration of change of the electro-physical quantity computed by the acceleration measurer.

Preferably, the determination by the determiner is performed by comparing the acceleration with a predetermined threshold value.

Preferably, the analyzer further comprises a receptacle mount portion to which a receptacle for receiving the sample is removably mounted, and the measurer measures an electro-physical quantity of the sample received by the receptacle mounted to the receptacle mount portion.

Preferably, the measurer comprises a current measuring circuit, and the analyzer further comprises a processor for analyzing the sample based on a current measured by the current measuring circuit.

Preferably, the acceleration measurer computes an acceleration of change of the current measured by the current measuring circuit.

Preferably, the acceleration measurer computes velocities at which the current changes at two time points and then computes an acceleration of the current change at an intermediate time point between the two time points based on the difference between the velocities of the current change at the two time points.

Preferably, the processor determines that the predetermined condition is not satisfied by comparing the acceleration of the current change computed by the acceleration measurer with a predetermined threshold value.

According to a fourth aspect of the present invention, there is provided an analyzer comprising a mount portion for removably mounting a sensor including a reagent layer which effects a predetermined reaction with a sample introduced to the reagent layer and a pair of electrodes for applying voltage to the reagent layer, a current measurer for measuring a current flowing between the electrodes when a voltage is applied across the electrodes, and a processor for performing analysis of the sample based on the current measured by the current measurer. The analyzer further comprises an acceleration measurer for computing an acceleration of change of the current at a time point when the current reaches a predetermined value after the sample is introduced to the reagent layer, and the processor determines whether or not a predetermined condition necessary for performing the analysis of the sample is satisfied by comparing the acceleration computed by the acceleration measurer with a predetermined threshold value.

With the analyzer having such a structure, the fail judging method provided in accordance with a first aspect or a second aspect of the invention can be performed properly, and the same advantages as described above can be obtained.

Other features and advantages of the present invention will become clearer from the description of the embodiments of the invention given below.

BRIEF DESCRIPTION OF THE DRAWINGS

FIG. 5A is a time chart of voltage applied across the electrodes of the biosensor, whereas

BEST MODE FOR CARRYING OUT THE INVENTION

Preferred embodiments of the present invention will be described below with reference to the accompanying drawings.

Figure 1:
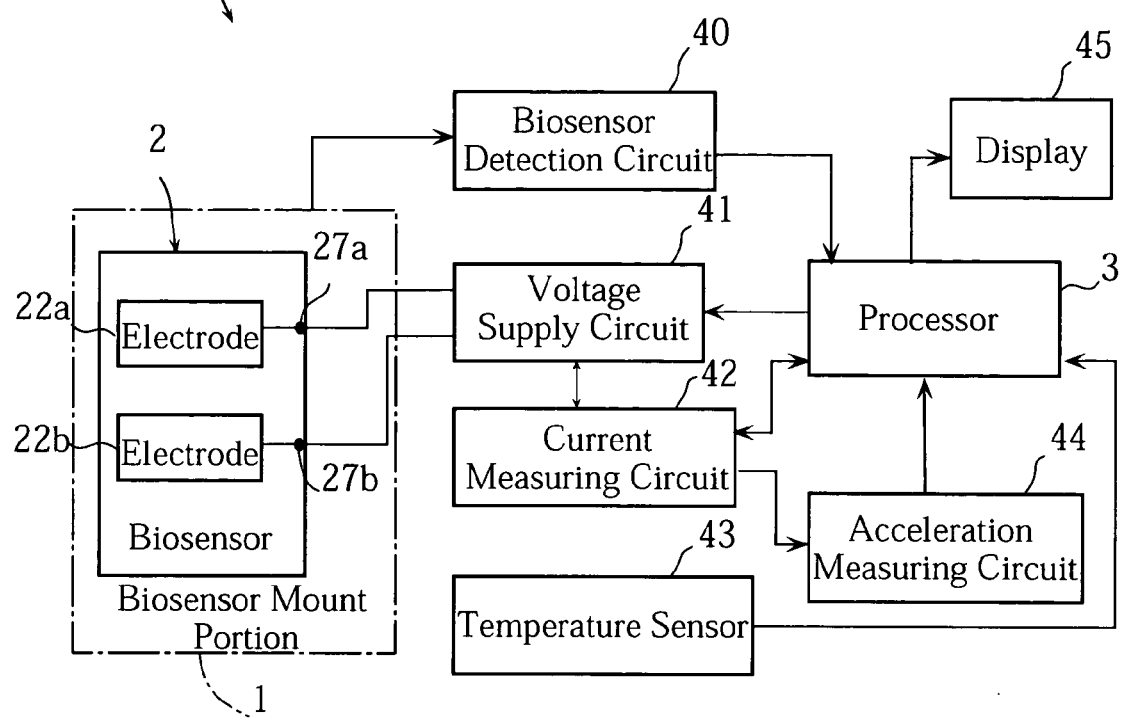
FIG. 1 is a circuit block diagram showing an example of analyzer according to the present invention.
Figure 2:
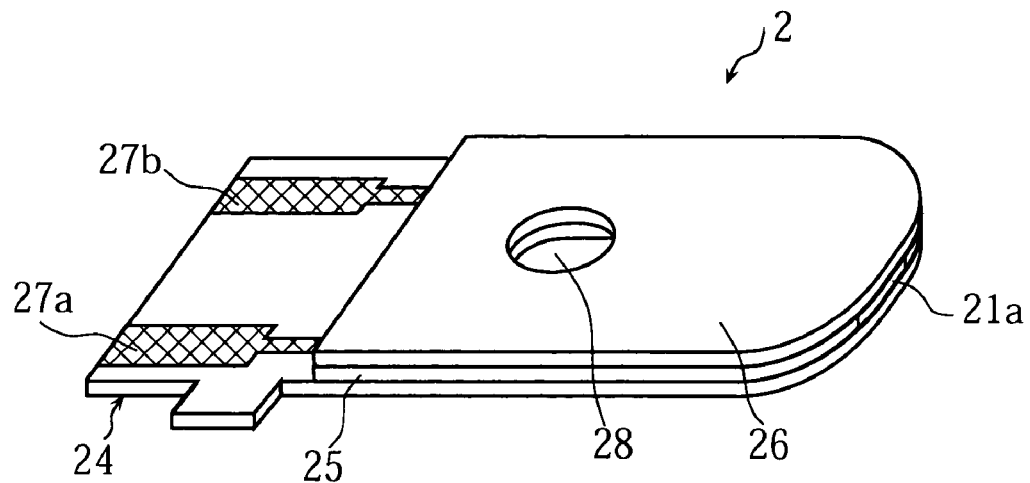
FIG. 2 is a perspective view showing an example of biosensor.
Figure 3:
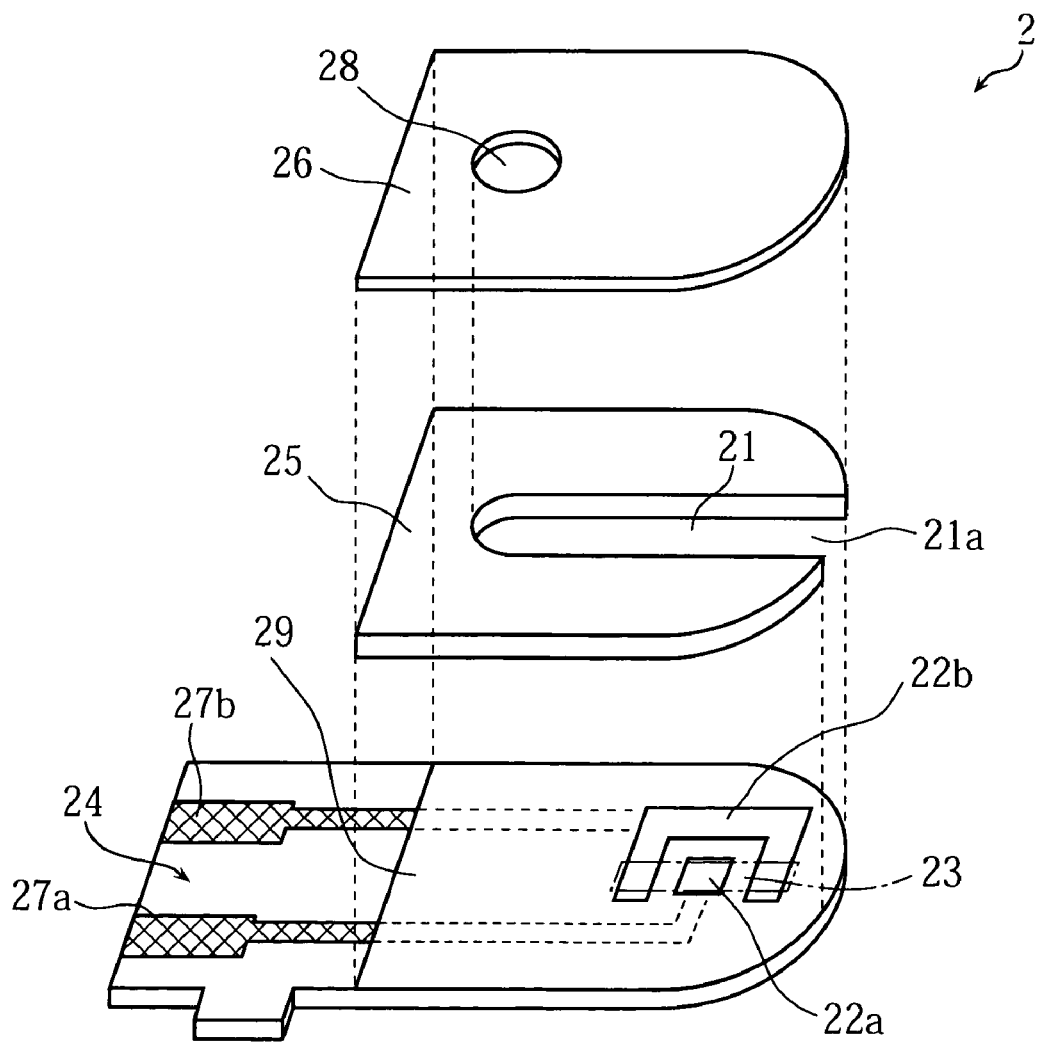
FIG. 3 is an exploded perspective view of the biosensor shown in FIG. 2.

FIG. 1 shows an embodiment of analyzer according to the present invention. A biosensor 2 as shown in FIGS. 2 and 3 is utilized for the analyzer A of this embodiment.

The biosensor 2, which functions to receive a sample, is an example of receptacle of the present invention. The biosensor 2 includes a substrate 24 having an upper surface on which a pair of electrodes 22a and 22b, and a reagent layer 23 are provided. The reagent layer 23 is arranged to cover respective upper surfaces of the electrodes 22a and 22b collectively or individually. The reagent layer 23 contains glucose oxidase and potassium ferricyanide as components to react with glucose in blood, for example. Portions around the reagent layer 23 and the electrodes 22a, 22b are covered with an insulating film 29. Aside of the insulating film 29 is provided terminals 27a and 27b electrically connected to the electrodes 22a and 22b.

On the substrate 24, a spacer 25 and a cover 26 are laminated. The spacer 25 is formed with a narrow slit 21 having a front end opening 21a. When a sample in the liquid state is applied to the front end opening of the slit, the sample travels toward a deeper portion in the slit 21 by capillary action and introduced to the reagent layer 23. To realize proper capillary action, the cover 26 is formed with a hole 28 which allows part of the slit 21 to communicate with the outside.

As shown in FIG. 1, the analyzer A in this embodiment includes a biosensor mount portion 1, a processor 3, a biosensor detection circuit 40, a voltage supply circuit 41, a current measuring circuit 42, a temperature sensor 43, an acceleration measuring circuit 44 and a display 45.

The biosensor mount portion 1 is an example of receptacle mount portion of the present invention and so structured that the biosensor 2 can be removably mounted to the biosensor mount portion. When the biosensor 2 is mounted to the biosensor mount portion 1, the terminals 27a and 27b of the biosensor 2 are electrically connected to the voltage supply circuit 41. The processor 3, which may comprise a CPU and an appropriate memory connected thereto, performs operation control at each of the units and data processing, which will be described later. The voltage supply circuit 41 applies a predetermined voltage across the paired electrodes 22a and 22b of the biosensor 2 under the control of the processor 3. The current measuring circuit 42 measures the current between the electrodes 23a and 22b and outputs the measurement data to the processor 3 and the acceleration measuring circuit 44.

The acceleration measuring circuit 44 functions to compute the acceleration of change of the current flowing between the electrodes 22a and 22b based on the current values measured by the current measuring circuit 42. The method of computing the acceleration will be described later in detail. The acceleration measuring circuit 44 may be provided as an integral part of the processor 3. The biosensor detection circuit 40 detects the biosensor 2 when the biosensor is properly mounted to the biosensor mount portion 1 and outputs a signal to that effect to the processor 3. The temperature sensor 43 measures the ambient temperature of the biosensor 2 and outputs the measurement data to the processor 3. The display 45 can display an intended image under the control of the processor 3 and may comprise a liquid crystal display or a CRT, for example.

Figure 4:
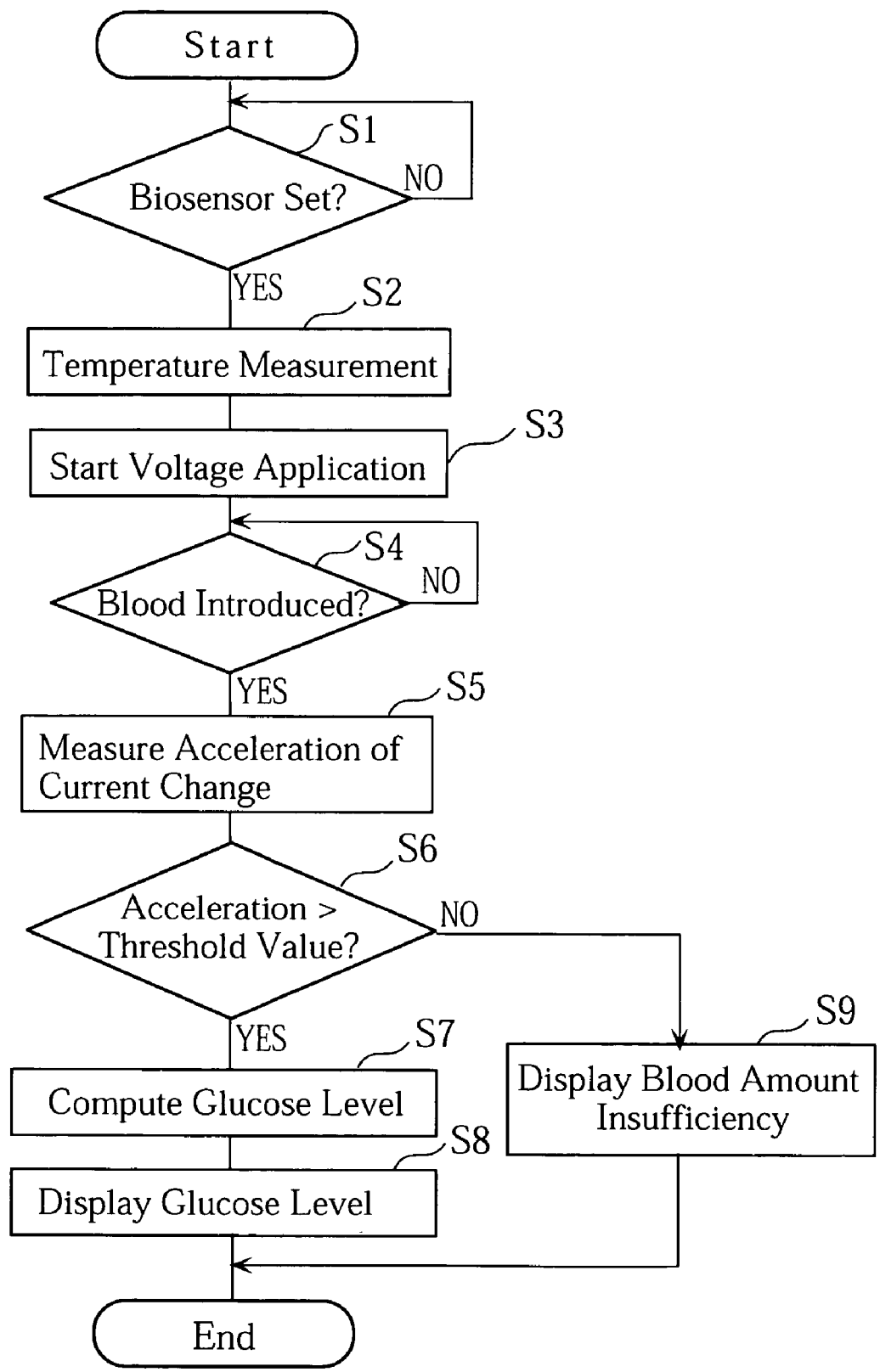
FIG. 4 is a flowchart showing the control operation by the processor of the analyzer shown in FIG. 1.

Next, referring to the flowchart shown in FIG. 4, description will be made of the analysis process using the biosensor 2 and the analyzer A, the manner of fail determination in the analysis process, and the operation of the processor 3. In this embodiment, the measurement of the glucose level in sampled blood will be exemplarily described.

Figure 5A:
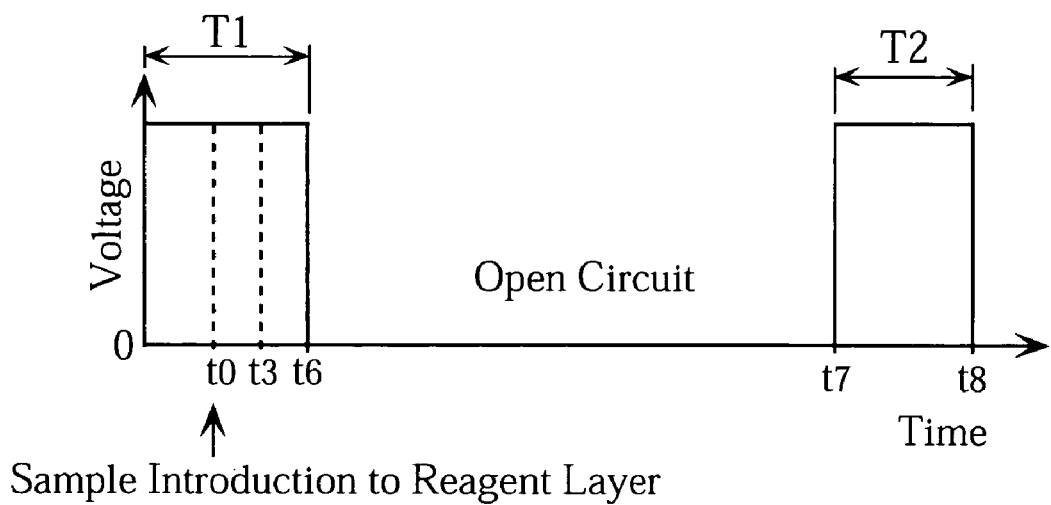

First, when the biosensor 2 is mounted to the biosensor mount portion 1 and the mounting is detected by the biosensor detection circuit 40 (S1: YES), the temperature sensor 43 measures the temperature and the temperature data is stored in the processor 3 (S2). The temperature data will be utilized later for temperature compensation of the glucose level measurement. Subsequently, the processor 3 drives the voltage supply circuit 41 to apply a voltage of e.g. about 500 mV across the electrodes 22a and 22b of the biosensor 2 (S3). Specifically, as shown in FIG. 5A, voltage is applied across the electrodes 22a and 22b twice, i.e. for a period T1 and for a period T2. As will be described later, the first voltage application for the period T1 is performed for the fail determination, whereas the second voltage application for the period T2 is performed for the glucose level measurement.

Figure 5B:
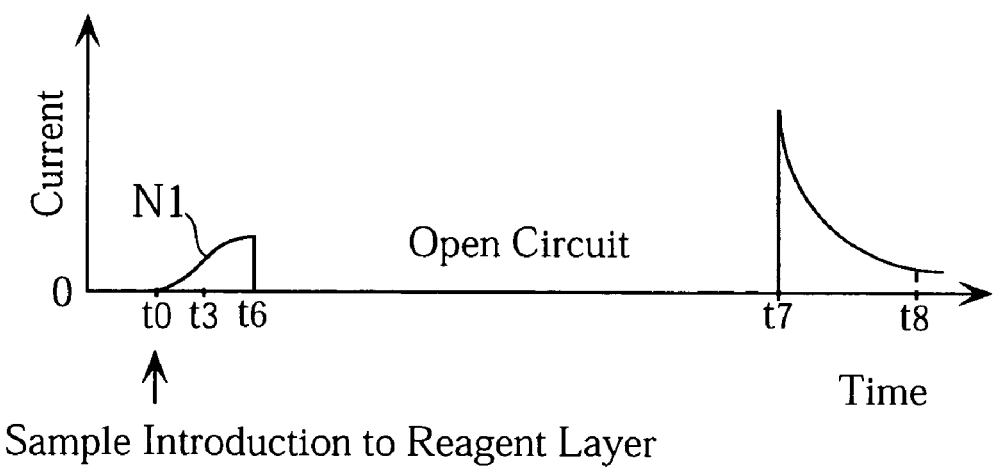
FIG. 5B is a time chart of current flowing between the electrodes of the biosensor.

When blood is introduced to the reagent layer 23 of the biosensor 2, electrical conduction is established between the electrodes 22a and 22b. Therefore, as indicated by the curve designated by the reference sign N1 in FIG. 5B, the current between the electrodes 22a and 22b continues to increase after the blood is introduced at the time point t0. When the reagent dissolves due to the introduction of the blood to the reagent layer 23, a liquid phase reaction system is established. At this time, electrons are released from glucose in the blood by the action of glucose oxidase as oxidoreductase, whereby glucose is oxidized. The electrons are transferred to potassium ferricyanide as an oxidized electron carrier, whereby potassium ferricyanide is reduced to potassium ferrocyanide. When a voltage is applied in this state, potassium ferrocyanide is oxidized to its original state, i.e., potassium ferricyanide, and electrons released in the reaction are supplied to the paired electrodes 22a and 2b, whereby current is detected between the electrodes 22a and 22b.

Figure 6:
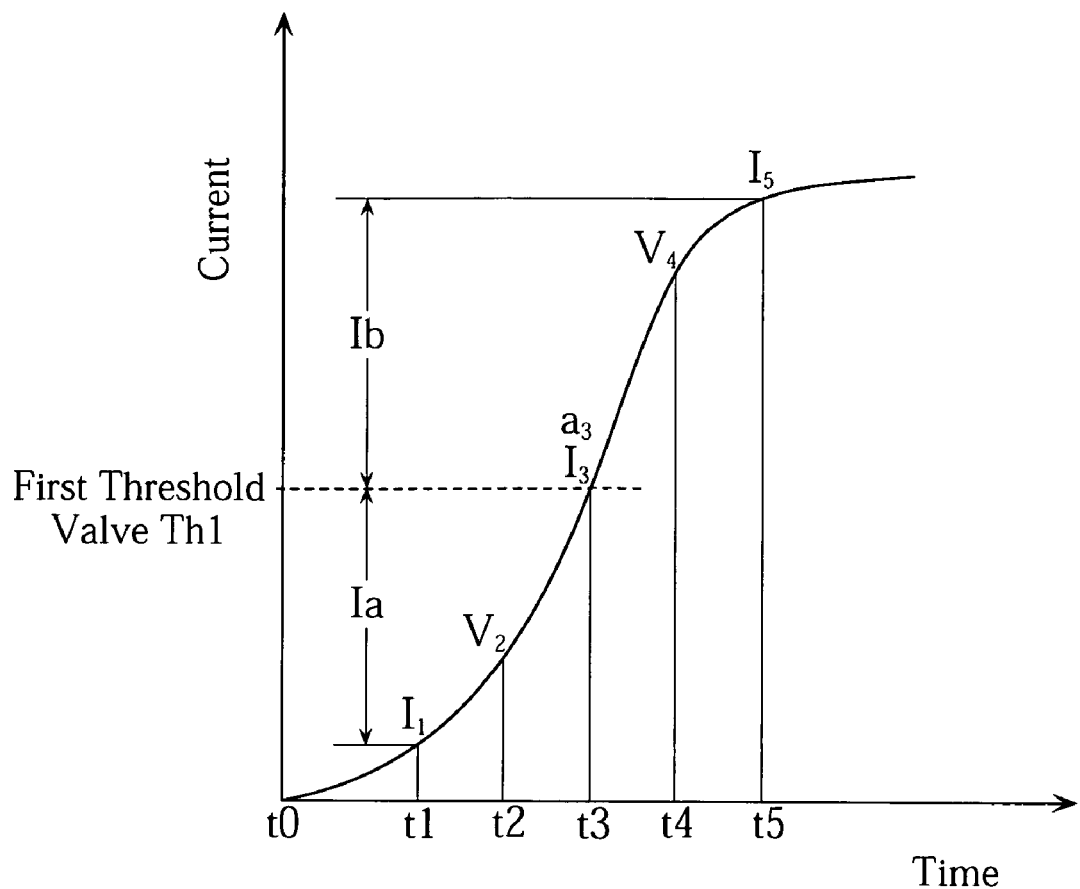
FIG. 6 illustrates the change of the current.

FIG. 6 illustrates the change of the current. At the time point when the current has reached a predetermined first threshold value Th1, the processor 3 determines that the blood was introduced (S4: YES). This time point t3 is set as a reference time point for the fail determination. The current measuring circuit 42 continues to measure the current, and the acceleration measuring circuit 44 computes the acceleration of the current change at the reference time point t3 based on a current value $I_3$ at the time point t3 (which is equal to the first threshold value Th1), and respective current values $I_1$ and $I_5$ at time points t1 and t5 which are slightly (e.g. about 0.2 seconds) before or after the time point t3 (S5).

Specifically, since the time interval between the time points t1 and t3 is short, the slope of the curve of the current at an intermediate time point t2, i.e., the rate $V_2$ of the current change at the time point t2 is computed by dividing the difference Ia between the current value $I_1$ at the time point t1 and the current value $I_3$ at the time point t3 by the time interval between the time points t1 and t3. Similarly, the rate $V_4$ of the current change at an intermediate time point t4 is computed by dividing the difference Ib between the current values at the time point t3 and t5 by the time interval between the time points t3 and t5. Subsequently, the difference between the rate of the current change $V_2$ at the time point t2 and the rate of the current change $V_4$ at the time point t4 is divided by the time interval between these time points, whereby the acceleration $a_3$ of the current change at the reference time point t3 is computed.

When the acceleration $a_3$ is computed, the processor 3 compares the acceleration $a_3$ with a predetermined second threshold value. When the acceleration $a_3$ is found to be no larger than the second threshold value as a result of the comparison (S6: NO), the processor 3 determines that the amount of blood introduced to the reagent layer 23 is insufficient and causes the display 45 to display a notice to that effect (S9). The processor then ends the process. Through experiments by the inventors of the present invention, it is confirmed that, in the case where the amount of introduced blood is insufficient, not only the rate of the current change but also the acceleration of the current change becomes relatively small as compared with the case where the amount of introduced blood is sufficient. Therefore, when the acceleration of the current change at a predetermined time point does not reach a predetermined value, it can be concluded that the amount of introduced blood is insufficient.

Figure 7:
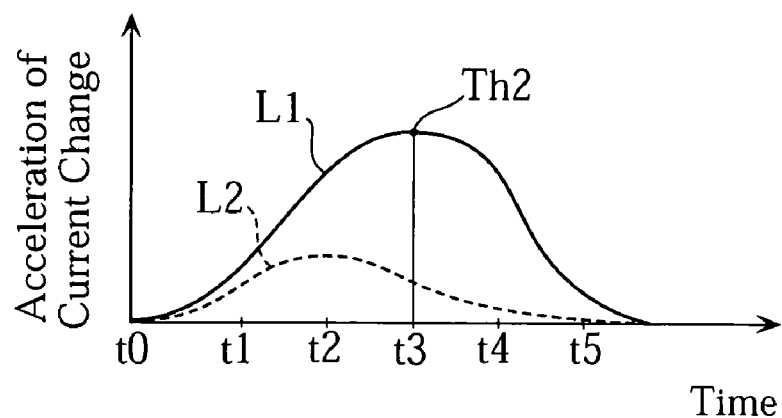
FIG. 7 illustrates the acceleration of the change of the current.
Figure 8:
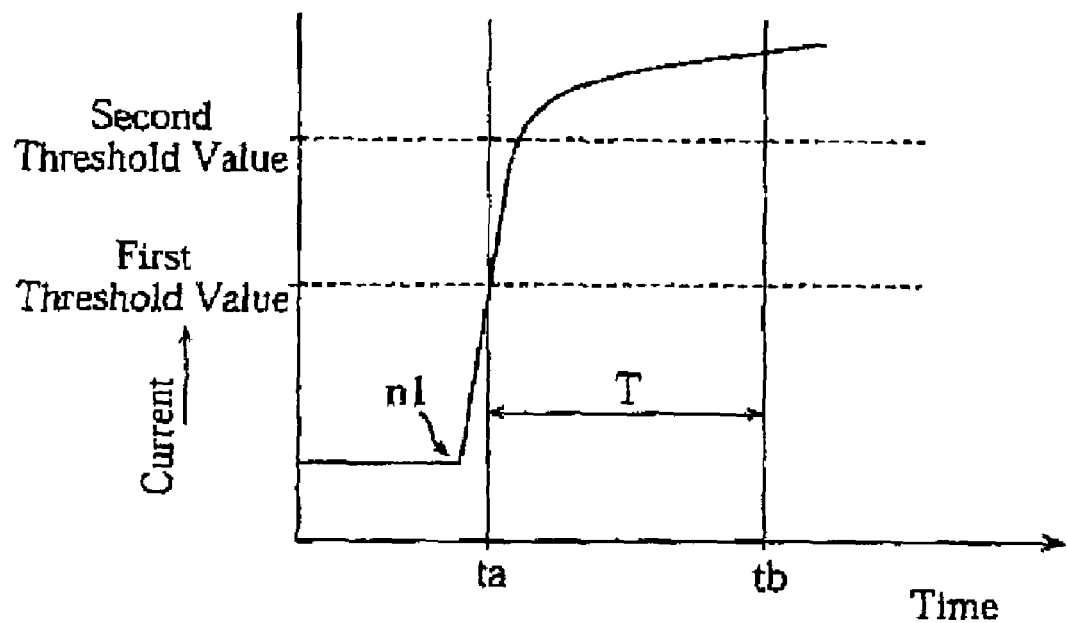
FIG. 8 illustrates a prior art method.

Specifically, the acceleration of the current change when the minimum amount of blood necessary for the accurate glucose level measurement is introduced is graphically represented by the curve indicated by the reference sign L1 in FIG. 7. On the other hand, the acceleration of the current change when the amount of introduced blood is insufficient is graphically represented by the dashed curve indicated by the reference sign L2 in the figure. As is clear from the figure, the acceleration of the current change in the case where the amount of introduced blood is insufficient is smaller over a relatively long period after the time point t0 than in the case where the amount of introduced blood is sufficient. The difference of the acceleration between the two cases is remarkable particularly at or around the time point at which the acceleration of the current change in the case where the amount of introduced blood is sufficient becomes maximum.

The maximum value Th2 of the acceleration in the curve L1, which is reached at the time point t3, is utilized as the above-noted second threshold value. Therefore, when the acceleration $a_3$ of the current change at the time point t3, which is computed by the acceleration measuring circuit 44, is smaller than the second threshold value Th2, it is determined that the amount of introduced blood is insufficient. The acceleration $a_3$ of the current change at the time point t3 is a value in a period in which the current varies largely in response to even a slight change of the amount of introduced blood. Therefore, when the amount of introduced blood is insufficient, the acceleration $a_3$ exhibits a value far below the second threshold value Th2. Thus, the insufficiency of the amount of introduced blood can be detected accurately. In this method, therefore, an excessively large value need not be set as the second threshold value Th2. Therefore, it is possible to lessen the possibility that the amount of introduced blood is erroneously determined to be insufficient although it is in fact sufficient.

When the acceleration $a_3$ at the time point t3 is larger than the second threshold value Th2 (S6: YES), the processor 3 performs control for the glucose level measurement (S7) and performs operation to cause the display 45 to display the result (S8). As the method for measuring the glucose level, any of conventionally known methods may be utilized, and one of such methods will be described below. First, as shown in FIG. 5A, at a time point t6 after a predetermined period (e.g. one second) has elapsed since the time point t3, voltage application across the electrodes 22a and 22b is interrupted so that the reaction of glucose in blood with the reagent layer 23 is promoted. Thereafter, at a time point t7 after a predetermined period (e.g. 25 seconds) has elapsed thereafter, voltage application across the electrodes 22a and 22b is restarted. Subsequently, at a time point t8 after a predetermined period (e.g. five seconds) has elapsed since the time point t7, the current between the electrodes 22a and 22b is measured and the glucose level is figured out based on the measurements.

The present invention is not limited to the foregoing embodiment. The specific structure of each step of the fail determination method in the analysis process may be modified in various ways. Similarly, the specific structure of each part of the analyzer according to the present invention may be modified in various ways.

For instance, in the present invention, instead of computing the acceleration of the current change at a single time point, accelerations at a plurality of time points may be computed. In this case, it may be determined that a fail condition exists when at least one of the accelerations is no larger than a predetermined threshold value. Further, acceleration at any time point may appropriately be utilized for the fail determination. In the present invention, instead of comparing an acceleration value of the current change as it is with a predetermined threshold value for the fail determination, the acceleration value of the current change or the threshold value may appropriately be corrected in view of the ambient temperature or other conditions, and the fail determination may be performed based on the corrected value.

The acceleration of the current change varies depending on not only the amount of the sample introduced to the reagent layer but also other conditions of each electrode or the reagent layer. Therefore, the acceleration of the current change may become smaller than the threshold value due to such other conditions. The fail determination method according to the present invention can also detect a failure in such a case. Therefore, with the fail determination method according to the present invention, it is possible to determine whether or not the conditions necessary for performing the analysis are satisfied as well as whether or not the amount of the sample introduced to the reagent layer is sufficient.

In the present invention, the electro-physical quantity of the sample to be measured is not limited to current, and other electro-physical quantities such as voltage or variation of charge may be utilized. As the reagent layer, use may be made of one that reacts with cholesterol or lactic acid for measuring the concentration of these components.

In the sample analysis, the reagent layer may not be used. Therefore, instead of the above-noted biosensor, a member which is not provided with a reagent layer may be used as the receptacle for receiving the sample. Moreover, the receptacle itself may not be provided with a terminal for measuring current, for example.

The invention claimed is:

1. A fail judging method to determine whether or not a predetermined condition necessary for performing analysis of a sample is satisfied by measuring an electro-physical quantity of the sample;
    wherein the method comprises computing an acceleration of change of the electro-physical quantity and determining, based on the acceleration, whether or not a required amount of the sample necessary for performing the analysis is supplied.

2. The fail judging method according to claim 1, wherein the electro-physical quantity is a current that flows when a voltage is applied to the sample.

3. A fail judging method to determine whether or not a predetermined condition necessary for performing analysis of a sample is satisfied, the analysis comprising: causing the sample to react with a predetermined reagent while applying a voltage to the sample and the reagent to cause a current to flow and computing a concentration of a particular component in the sample based on the current, wherein the method comprises:
    computing an acceleration of change of the current at a time point at which the current reaches a predetermined value after the sample is introduced to the reagent layer; and
    determining, based on the acceleration, whether or not a required amount of the sample necessary for performing the analysis is supplied.

4. The fail judging method according to claim 3, wherein the determination step comprises comparing the acceleration with a predetermined threshold value and determining that the required amount of the sample is not supplied when the acceleration is smaller than the threshold value.

5. An analyzer provided with a measurer for measuring an electro-physical quantity of a sample,
    wherein the analyzer comprises:
    an acceleration measurer configured for computing an acceleration of change of the electro-physical quantity; and
    a determiner configured for determining, based on the acceleration computed by the acceleration measurer, whether or not a required amount of the sample necessary for performing analysis is supplied.

6. The analyzer according to claim 5, wherein the determination by the determiner is performed by comparing the acceleration with a predetermined threshold value.

7. The analyzer according to claim 5, further comprising a receptacle mount portion to which a receptacle for receiving the sample is removably mounted, wherein the measurer measures an electro-physical quantity of the sample received by the receptacle mounted to the receptacle mount portion.

8. The analyzer according to claim 5, wherein the measurer comprises a current measuring circuit, and wherein the analyzer further comprises a processor for analyzing the sample based on current measured by the current measuring circuit.

9. The analyzer according to claim 8, wherein the acceleration measurer computes an acceleration of change of the current measured by the current measuring circuit.

10. The analyzer according to claim 9, wherein the acceleration measurer computes velocities at two time points at which the current changes and then computes an acceleration of the current change at an intermediate time point between the two time points based on a difference between the velocities of the current change at said two time points.

11. An analyzer comprising: a mount portion for removably mounting a sensor including a reagent layer which effects a predetermined reaction with a sample introduced to the reagent layer, and a pair of electrodes for applying a voltage to the reagent layer;

a current measurer for measuring a current flowing between the electrodes when a voltage is applied across the electrodes; and a processor for performing analysis of the sample based on the current measured by the current measurer;

wherein the analyzer further comprises an acceleration measurer configured for computing an acceleration of change of the current at a time point when the current reaches a predetermined value after the sample is introduced to the reagent layer; and wherein the processor is configured to determine whether or not a required amount of the sample necessary for performing the analysis is supplied, the determination being made by comparing the acceleration computed by the acceleration measurer with a predetermined threshold value.

* * * * *